US005698162A

United States Patent [19]

Belly et al.

[11] Patent Number: 5,698,162

[45] Date of Patent: Dec. 16, 1997

[54] APPARATUS FOR STAINING OF CELLS AND TISSUES

[75] Inventors: Robert Troconis Belly; John Benjamin Chemelli, both of Webster; Michele McWilliams Steinmann, Rochester, all of N.Y.

[73] Assignee: Johnson & Johnson Clinical Diagnostics, Rochester, N.Y.

[21] Appl. No.: 792,414

[22] Filed: Feb. 3, 1997

Related U.S. Application Data

[60] Provisional application No. 60/015,532, Feb. 27, 1996.

[51] Int. Cl.$^{6}$ .......... G01N 21/03

[52] U.S. Cl. .......... 422/58; 422/61; 422/100; 422/102

[58] Field of Search .......... 422/56, 58, 61, 422/102–103, 99–101; 435/288.3–288.5

[56] References Cited

U.S. PATENT DOCUMENTS 4,541,987 9/1985 Guadagno .......... 422/58
5,147,606 9/1992 Charlton et al. .......... 422/58

*Primary Examiner*—Lyle A. Alexander
*Attorney, Agent, or Firm*—Dana M. Schmidt

[57] ABSTRACT

A slide for reacting a biological sample with reagents, and a method for using the same. The slide comprises a liquid-impervious top surface comprising glass, first portions of the surface having thereon a hydrophobic mask that repels an aqueous liquid, and second portions of the surface being completely free of any coverage by the mask so as to be wettable with an aqueous liquid, at least one of the other wettable second portions being totally isolated from the other wettable second portions by some of the mask, so that aqueous liquid will not flow from the one wettable portion to the another wettable portion until an overflow amount of aqueous liquid is added to the one wettable portion in an amount sufficient to bridge across the mask, and an absorbent material mounted at one side of the surface in position to receive liquid from the slide. The method of use features confining aqueous reagents to the area restricted by the hydrophobic mask, except for when additional amounts are added to force at least some of the liquid to move towards a side edge of the slide, where most of the liquid is absorbed.

9 Claims, 5 Drawing Sheets

40
12
10
22
20
20'
20"
16
16'
16"
18
18'
18"
30
D1
D2
W
X3
t
II
D1 > D2

APPARATUS FOR STAINING OF CELLS AND TISSUES

This application claims the benefit of U.S. Provisional Application No. 60/015,532, filed Feb. 27, 1996, now abandoned.

FIELD OF THE INVENTION

This invention relates to a glass slide and method of using it, particularly for detecting sample antigens such as by immunostaining cells.

BACKGROUND OF THE INVENTION

In wet assay analyzers, it has been customary to provide liquid reagents in bottles, and then to aspirate out reagents into pipettes which dispense them into cuvettes containing patient sample, or onto some other kind of sample support. One problem among others is that the reagent bottles are supplied with an overabundance, and once opened, tend to have only a finite useful lifetime. As a result, excess, unused reagent has to be thrown out when an opened bottle ages past its posted lifetime. This is particularly a problem for expensive reagents, such as antibodies.

Yet another problem with such analyzers has been their unsuitability for handling cell-staining operations, given the fact that cell-staining is usually done on glass slides. Although U.S. Pat. No. 3,654,091 to Binnings discloses an analyzer for processing glass slides, it does so using the unsatisfactory bottled reagent concept described in the previous paragraph.

Furthermore, cell-staining on glass slides has a background problem. If the cell-staining area is allowed to dry out, a high amount of background color tends to form. Since some kind of blotting is customarily done to remove wash fluid, drying-out is almost inevitable, given that the staining reagents have to stand or incubate for a period of time on the slide. Hence, it has been a problem with conventional glass slides that high background due to drying, has occurred during cell-staining. Stated in other words, there has been a need prior to this invention, to provide a glass slide for cell-staining that somehow does not completely dry out in the staining area, that is, liquid does not completely flow away from such areas, particularly during incubation.

SUMMARY OF THE INVENTION

We have devised a glass slide and method of use that solve the above-mentioned problems.

More specifically, there is provided, in accord with one aspect of the invention, a glass slide for reacting a biological sample with reagents, the slide comprising:

a hydrophobic mask over the entire exposed surface of the glass slide except at:

a) a sample-receiving area, b) two optional control areas, c) optionally a side edge of the slide and d) a removal channel surrounding the area a) as well as any area b), each channel being separated from its respective area a) or b) by a portion of the mask.

In accord with another aspect of the invention, there is provided a slide for reacting a biological sample with reagents, comprising:

a liquid-impervious top surface comprising of glass, first portions of the surface having thereon a hydrophobic mask that repels an aqueous liquid, and second portions of the surface being completely free of any coverage by the mask so as to be wettable with an aqueous liquid, at least one of the other wettable second portions being totally isolated from another of the other wettable second portions by some of the mask, so that aqueous liquid will not flow from the one wettable portion to another wettable portion until an overflow amount of aqueous liquid is added to the one wettable portion in an amount sufficient to bridge across the mask, and an absorbent material mounted at one side of the surface in position to receive liquid from the slide.

In accord with still another aspect of the invention, there is provided a method of producing a detectable reaction on a glass slide by adding reagents to a sample, the method comprising the steps of a) depositing a sample onto a restricted, wettable area of a glass slide, that is separated from all edges of the slide, b) depositing an aqueous solution of at least one reagent onto the restricted area while keeping the solution confined to the restricted area and away from the edges, c) incubating the reagent with the sample, d) thereafter, depositing additional aqueous solution onto the restricted area in an amount sufficient to force the solution to move away from the restricted area towards at least one of the side edges, and e) removing by absorbing into an absorbent, that portion of the solution that is forced towards the one side edge.

Accordingly, it is an advantageous feature of the invention that a glass slide is provided for cell-staining, which is coated with a mask in certain areas such that fluid flow is controlled and the cell-staining area is prevented from drying out.

It is a related advantageous feature of the invention that a cell-staining glass slide is provided that produces a reduced background color.

Other advantageous features will become apparent upon reference to the following "Detailed Description", when read in light of the attached drawings.

DETAILED DESCRIPTION OF THE INVENTION

The discussion hereinafter is of the preferred embodiments, wherein immunostaining of cells is done on a support comprising glass slides bearing a preferred hydrophobic mask of a particular configuration, and a preferred absorbent material. In addition, the invention is useful regardless of the type or configuration of the mask that is used, and regardless of the type of absorbent that is used, provided a portion of the unmasked slide remains isolated by the mask sufficiently to keep some liquid from flowing away, and thus to keep that portion from drying out.

Figure 1:
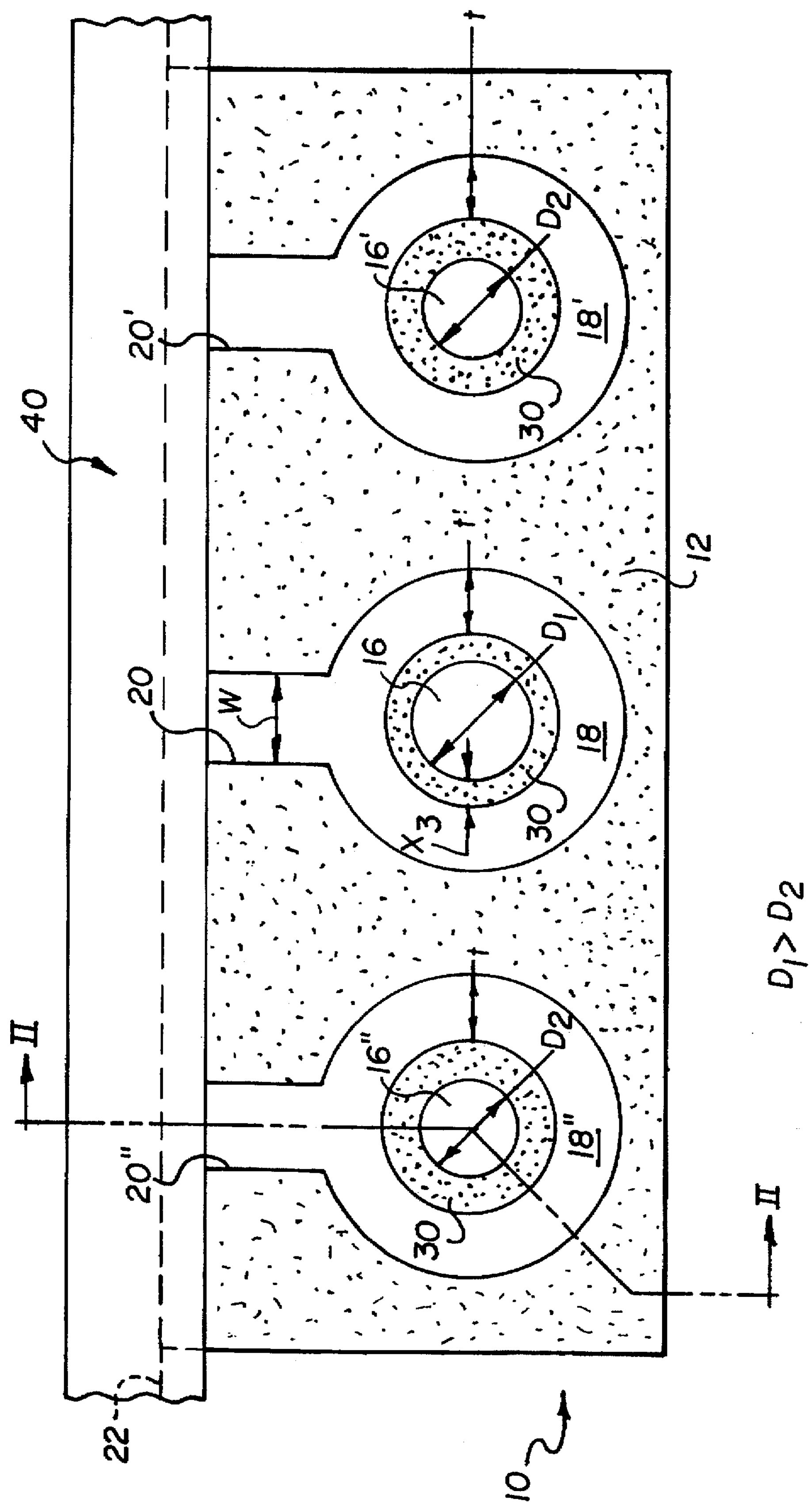
FIG. 1 is a plan view of a glass slide and its associated absorbent material, constructed in accordance with the invention.
Figure 2A:
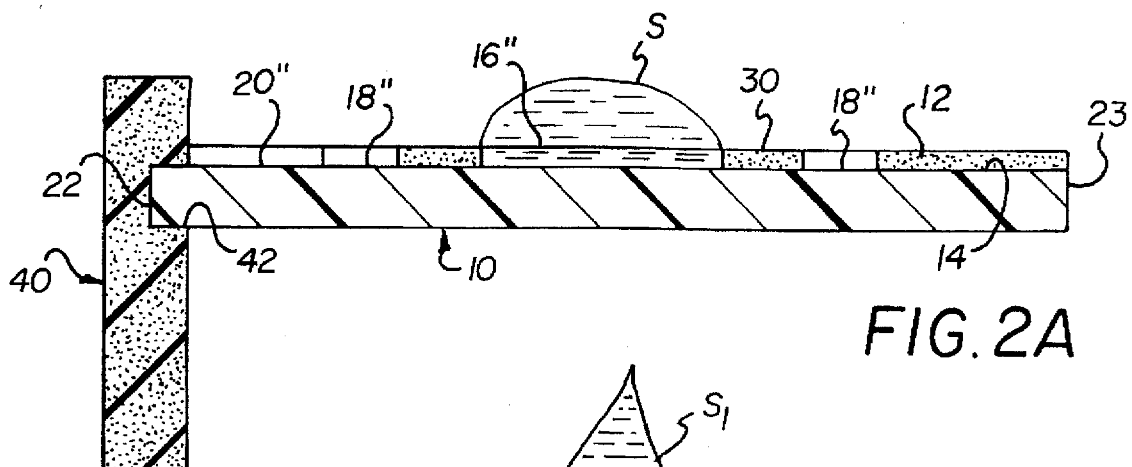
FIG. 2A is a section view taken along the line II—II of FIG. 1, showing a fluidized cell sample in place.

Thus, in accordance with the invention, a glass slide 10 is provided, FIG. 1, with a hydrophobic mask layer 12 on its top surface 14, FIG. 2A, coating the entire top layer except for the wettable areas 16,16',16"; 18,18',18", and optional side channels 20,20',20" that lead from areas 18,18',18" to a side edge 22 of the slide. This leaves opposite side edge 23 as a cantilevered edge. Most preferably, areas 16, 16', and 16" are circular in shape, with areas 18, 18', and 18" being annuli surrounding areas 16, 16', and 16", respectively, but spaced and separated therefrom by annuli 30 of the mask, FIG. 1. Side edge 22 is in turn held and engaged by an absorbent material such as rectangular slab 40, such as in a notch 42, FIG. 2A, of the slab.

Any hydrophobic material can be used for layer 12, provided it is sufficiently hydrophobic for the liquid deposited on the slide during use, to repel the liquid and confine the liquid to wettable areas. Highly preferred are materials such as polytetrafluoroethylene, available under the trademark "Teflon", and dimethyldichlorosilane which can be coated as described, for example, in UK Patent No. 2,125,183, the details of which are expressly incorporated herein by reference.

A useful thickness for layer 12 is about 0.025 mm.

Any aqueous-absorbing medium can be used for absorbent 40. For example, synthetic sponges made from, e.g., cellulose, can be used, as well as natural sponges from the sea. The absorbent need only have sufficient absorbing capacity as to absorb all the liquid that is deposited onto slide 10 during its expected use, described below. Most preferably, this is a volume to be absorbed that is no greater than about 15 mL.

Although the dimensions of circles 16,16',16" and annuli 18,18',18" and 30 can be varied, it is preferred that diameter $D_1$ of circle 16 exceed diameter $D_2$ of circle 16' and 16", as will be apparent from the use described below.

Figure 3:
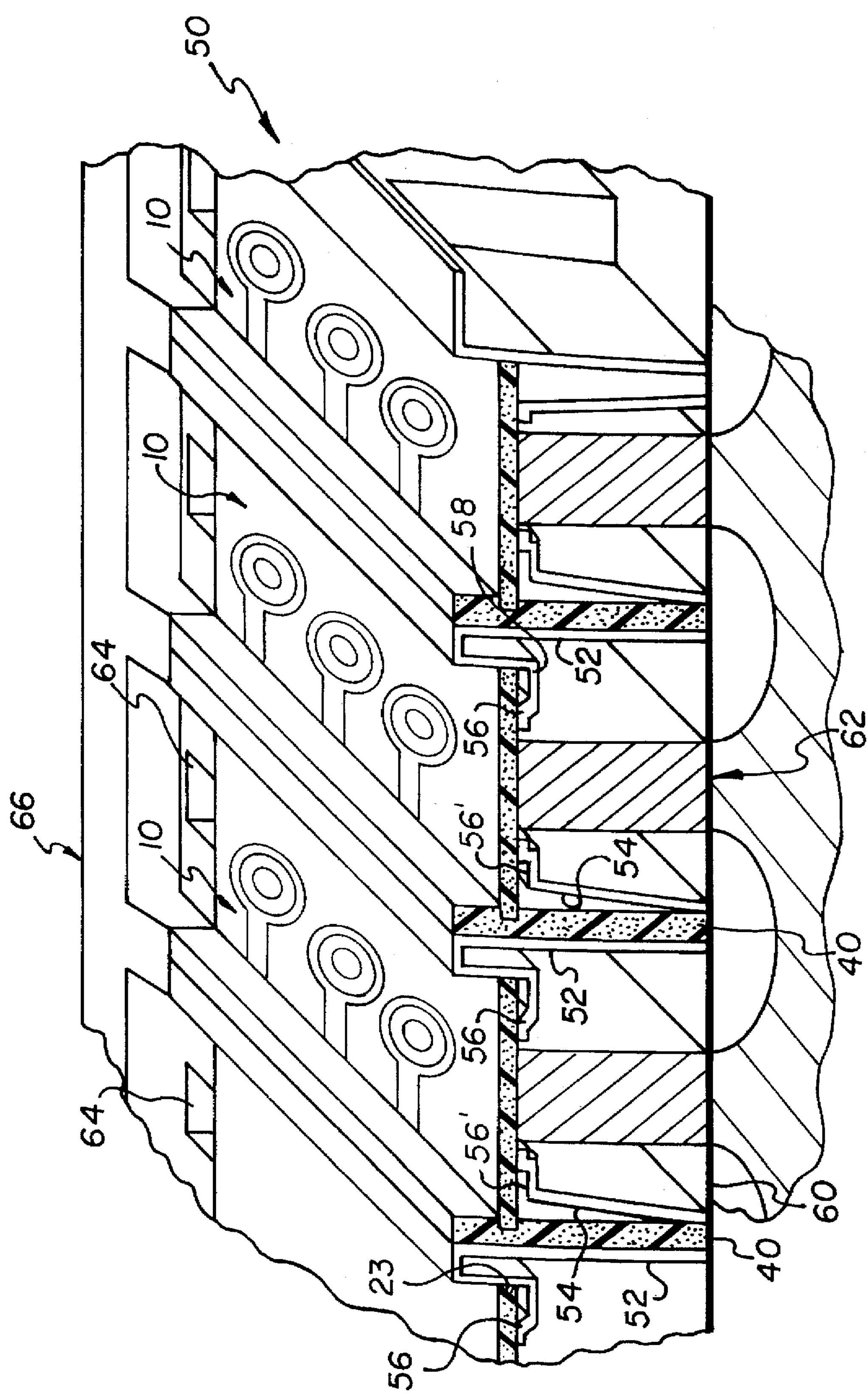
FIG. 3 is a fragmentary isometric view of apparatus for mounting a plurality of such slides and absorbent materials.

Most preferably, FIG. 3, each slide 10 and slab 40 is mounted in a support 50 which will hold a plurality of such slide-and-slab combinations side-by-side. More specifically, support 50 comprises plural frames 52 each of which is shaped with a trough 54 to hold slab 40, and two ledges 56,56' to hold the cantilevered edge 23 opposite to edge 22. Ledges 56,56' can be optionally provided with a drip trough 58 to receive liquid overflows, if any.

The frames 52 are then mounted on a plate 60, spaced far enough from the next adjacent frame to receive a slide-and-slab combination in the spacing between them. Optionally, a heating boss 62 extends upward from plate 60 to help support, and heat, each slide 10 in the combination (using a heating element, not shown).

Recesses 64 are preferably formed in a side shoulder 66 affixed to plate 60, the recesses providing finger access to the slide-and-slab combination.

A preferred use of the slide 10-and-slab 40 combination is for immunostaining, as follows, FIGS. 2A–2F, though other uses can be made:

First, a quantity of a sample, such as a tissue culture, is deposited onto area 16 of the slide, FIG. 1. If the sample has been parrafinized for storage, it is deparrafinized in a conventional manner, dehydrated in alcohol, and then washed. Areas 16' and 16", on the other hand, have deposited and fixed thereon, as positive and negative controls, suitable materials such as cell lines grown for this purpose, e.g., breast cancer cells (e.g., MCF-7 line), and small lung carcinoma cells (e.g., Calu 6 line).

Such a slide 10 so prepared is then immunostained by depositing sequentially, various aqueous materials onto the slide and then absorbing them into slab 40 to remove the excess. This is done by first allowing the various liquids to interact only at areas 16, 16' and 16", during an incubation period, and then to force them to move beyond the mask annulus 30 that protects and surrounds areas 16, 16', and 16", so as to contact, absorbent slab 40 to be absorbed.

More specifically, FIG. 2A, a first liquid S is deposited onto slide 10 at three separate places so as to contact and remain only within areas 16, 16', and 16". Such a liquid contains, e.g., a reagent such as a primary antibody to the cellular antigen of choice. The retention of liquid S in areas 16, 16', and 16" by mask annuli 30 serves to incubate the antibody solution with the sample, without drying out.

Figure 2B:
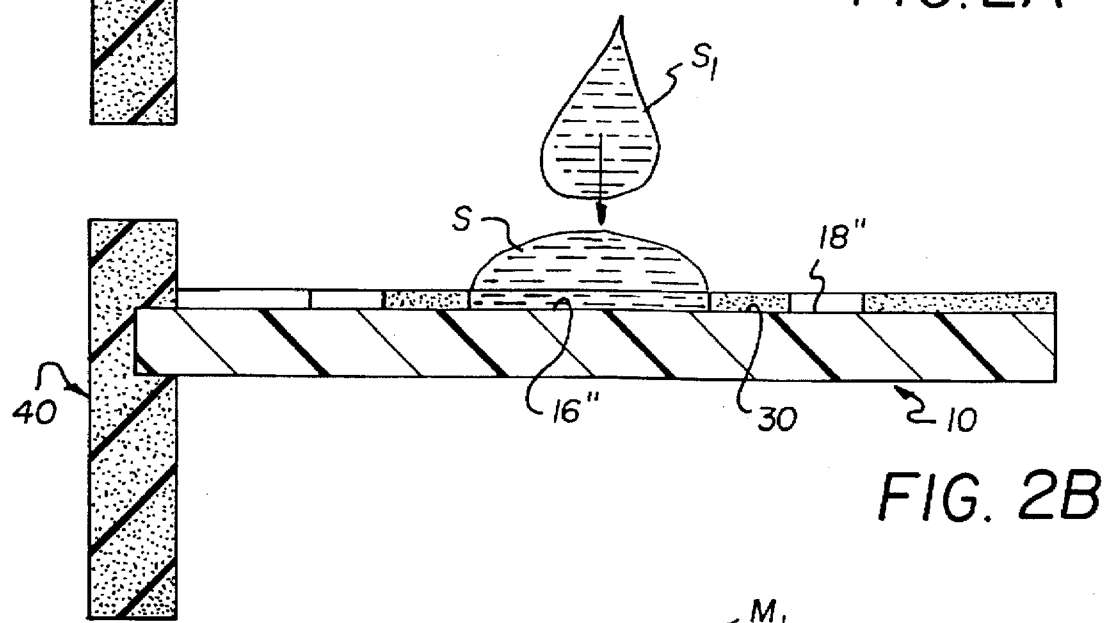
FIG. 2B–F are section views similar to that of FIG. 2A, except that wash fluid has been added as is done during use, illustrating how the meniscus is forced to overcome the mask barrier, FIG. 2C; then to flow out the channel to the absorbent material, FIG. 2E, with or without additional optional wash liquid, FIG. 2D; and then how the absorbent material absorbs the excess while leaving the stained area moist, FIG. 2F.
Figure 2C:
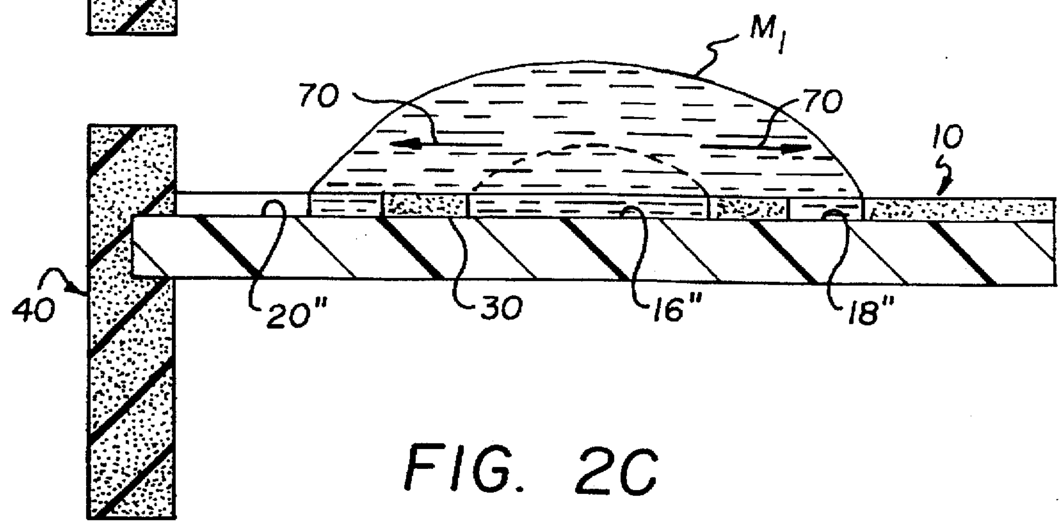

Thereafter, FIG. 2B, an additional, overflow amount, drop S', of aqueous liquid, such as the rinse, is added, to each of 16, 16', and 16", sufficient in amount to force the total liquid to "bridge" the hydrophobic barrier, arrows 70, presented by mask annulus 30, FIG. 2C, thereby wetting annular areas 18, 18', and 18", respectively. A useful amount of drop S' to force the bridging of the mask is, for areas 16' and 16", about 3 drops or 150 μL. For area 16, it is about 13 drops, or 650 μL. In time, the meniscus $M_1$, FIG. 2C, will spread out to cover channels 20, 20', and 20", FIG. 2E, and thus contact absorbent slab 40, arrow 72. Optionally an additional quantity S" of rinse liquid can be added, FIG. 2D, to aid in the spreading of meniscus $M_1$ into channels 20, 20', and 20".

Figure 2D:
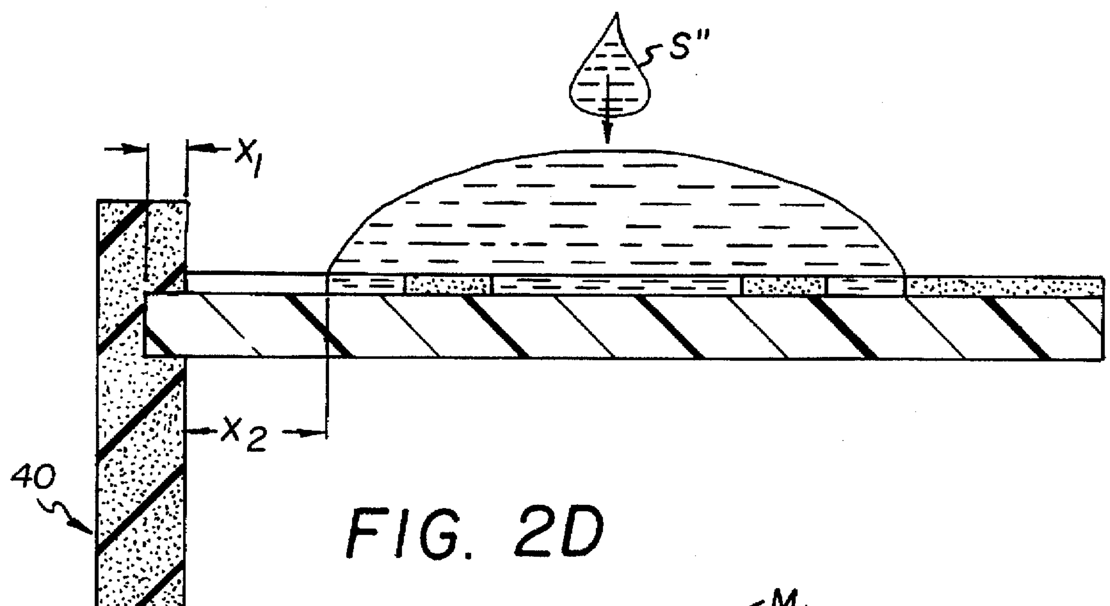
Figure 2E:
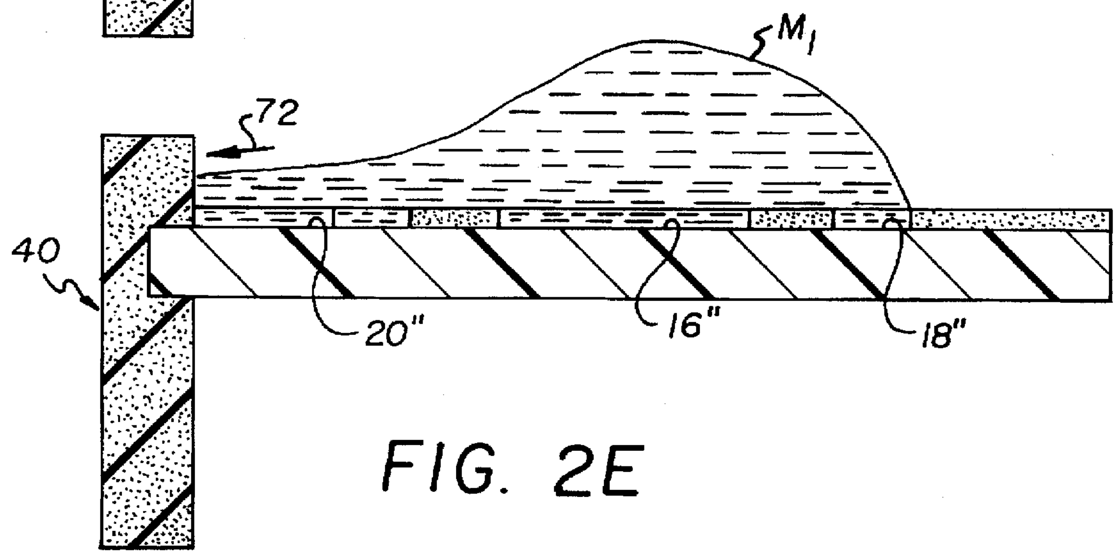
Figure 2F:
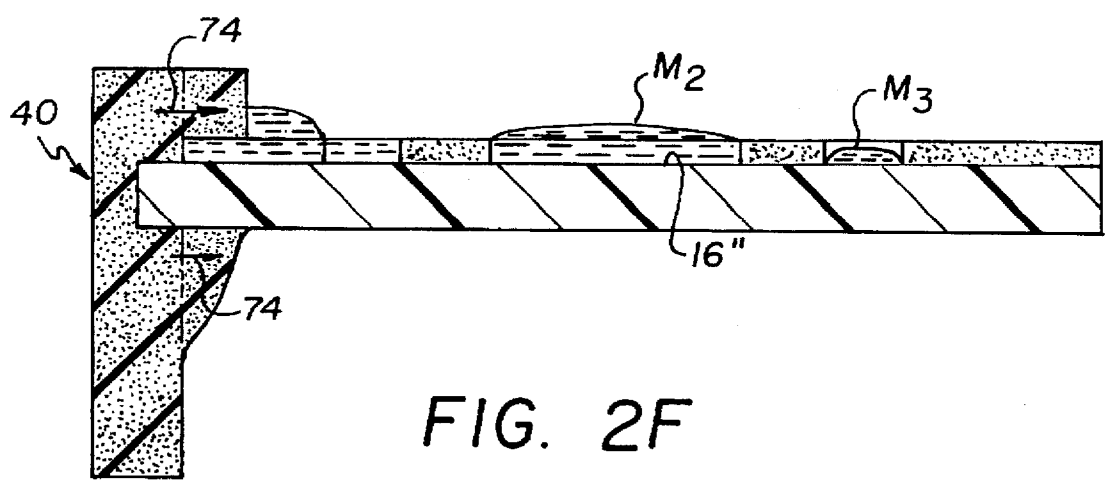

Slab 40 then receives and absorbs the liquid into it, swelling in the process, arrows 74, FIG. 2F, leaving only residual menisci $M_2$,$M_3$ on areas 16,16',16" and 18,18',18", respectively. However, the residual meniscus is sufficient to keep areas 16, 16', and 16" from drying out, because mask annuli 30 protects the liquid from being absorbed.

Thereafter, the process is repeated, but using the following liquids, all of which are conventional.

First, a link solution such as an anti-immunoglobulin solution is added to all three areas 16, 16', and 16", and thereafter spread out onto areas 18,18',18" and channels 20, 20', and 20", respectively. Thereafter a label solution, such as peroxidase, is added and spread. Thereafter, a solution of hydrogen peroxide is deposited and spread. Thereafter, or simultaneous with the hydrogen peroxide solution, a solution of a chromogen which is a substrate for the label, is deposited and spread.

This completes the staining process. Conventional "fixing" of the stains can then be done to each of the areas 16, 16', and 16".

Any method of depositing the liquids onto slide 10 can be used. A useful example is the use of a flexible cuvette containing the liquids in pre-packaged form as burstable compartments, and in particular, that described in commonly-owned co-pending application U.S. Ser. No. 60/005,467 [Docket No. CDS-76] filed on Oct. 16, 1995 and entitled "Container For Staining Of Cells And Tissues In Combination With A Roller And A Support".

When using the slide 10 in the preferred manner described above for immunostaining, the slab 40 is preferably provided with the following features:

When dimension $X_1$, FIG. 2D, is about 4 mm and dimension $X_2$ is about 5 mm, optimum removal of the excess liquid of about 1.5 mL per each rinse, into a slab 40 comprising a cellulose sponge, occurred. If on the other hand $X_1$ is 5 mm or more, the expansion, arrow 74, FIG. 2F, tended to push the sponge material out too far into the slide, e.g. into areas 16, 16', 16" or 30. If that happens, the sponge draws off too much liquid from the areas 16, 16' and/or 16".

(If the channel dimension $X_2$ is varied from the above value, it can be expected that the optimum value for $X_1$ may vary also.)

Also for the above immunostaining use, it is preferred that the width W of channels 20, 20', and 20", FIG. 1, be about 5 mm, and that the areas 16,16',16" be about 12 mm in diameter for 16 and 7 mm for 16' and 16". The thickness $X_3$ of mask annulus 30 is preferably about 2 mm, and wettable annular area 18 preferably has a width t of about 0.5–3.0 mm. For areas 18', 18", t is preferably about 2.5–3.0 mm.

It is not necessary that channels 20, 20', or 20" be used to draw the excess liquid into the absorbent slab. Instead, the slab can overhang the outer annuli, FIGS. 4 and 5. Parts similar to those previously described bear the same reference numeral, to which the distinguishing suffix "A" is appended.

Figure 4:
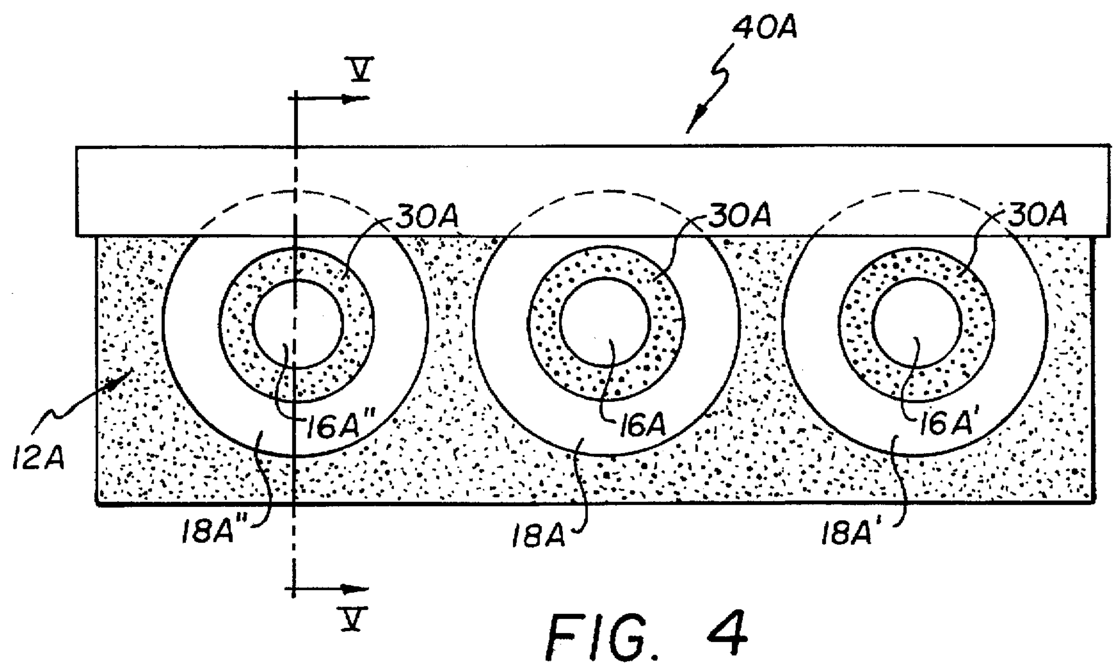
FIG. 4 is a plan view similar to that of FIG. 1, but of an alternate embodiment.
Figure 5:
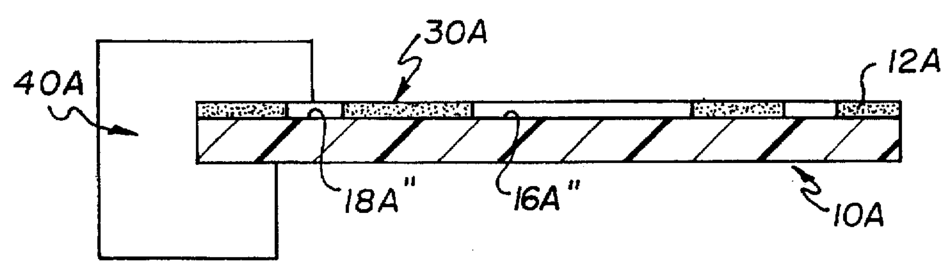
FIG. 5 is an elevational view in section, taken along the line V—V of FIG. 4.

Thus, slide 10A, FIG. 4, is coated with hydrophobic mask 12A except in areas 16A, 16A',16A" and annuli 18A, 18A',18A" separated from areas 16A, 16A',16A" by mask annuli 30A, respectively. Absorbent slab 40A holds the slide and extends out over the slide, all as described hereinbefore. However, there are no channels extending out of annuli 18A, 18A', or 18A". Instead, slab 40A overhangs sufficiently as to extend into the area of annuli 18A, 18A', and 18A", FIG. 5. Because of this overhang, liquid that bridges over mask 30A to contact annuli 18A, 18A', or 18A" will also contact and be received into absorbent slab 40A.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A glass slide for reacting a biological sample with reagents, said slide comprising:

a hydrophobic mask over the entire exposed surface of said glass slide except at a) a sample-receiving area, b) two optional control areas, c) optionally a side edge of said slide and d) a removal channel surrounding said area a) as well as any area b); and each said channel being separated from its respective area a) or b) by a portion of said mask.

2. A slide as defined in claim 1 and further including an absorbent material attached to said side edge, of sufficient porosity as to absorb liquid contacting said absorbent material from any and all of said areas a) and b).

3. A slide as defined in claim 2, wherein said absorbent is in contact with said removal channels.

4. A slide as defined in claim 1, in combination with a support for removably mounting a plurality of said slides side-by-side, said support including a plurality of walls constructed to receive said slides spaced apart from each other.

5. A slide for reacting a biological sample with reagents, comprising:

a liquid-impervious top surface comprising glass, first portions of said surface having thereon a hydrophobic mask that repels an aqueous liquid, and second portions of said surface being completely free of any coverage by said mask so as to be wettable with an aqueous liquid, at least one of said wettable second portions being totally isolated from another of said wettable second portions by some of said mask, said one wettable second portion being surrounded by said another wettable second portion;

so that aqueous liquid will not flow from said one wettable portion to said another wettable portion until an overflow amount of aqueous liquid is added to said one wettable portion in an amount sufficient to bridge across said mask; and an absorbent material mounted at one side of said surface in position to receive liquid from said slide.

6. A slide as defined in claim 5, wherein said absorbent material is separated from said wettable portions by at least one of said first portions of said hydrophobic mask, except for channels of said top surface that are unmasked.

7. A method of producing a detectable reaction on a glass slide by adding reagents to a sample, the method comprising the steps of:

a) depositing a sample onto a restricted, wettable area of a glass slide, that is separated from all edges of the slide;

b) depositing an aqueous solution of at least one reagent onto said restricted area while keeping said solution confined to said restricted area and away from said edges;

c) incubating said reagent with said sample;

d) thereafter, depositing additional aqueous solution onto said restricted area in an amount sufficient to force said solution to move away from said restricted area towards a wettable area separated from and surrounding said restricted area, and towards at least one of said side edges; and e) removing by absorbing into an absorbent, that portion of said solution that is forced towards said one side edge.

8. A method as defined in claim 7, wherein said slide is provided with a hydrophobic mask effective to restrict limited amounts of aqueous solution from flowing out of said restricted area, so that said removing step is ineffective in removing all of said solution from said slide.

9. A method as defined in claim 8, wherein said step e) comprises positioning an absorbent slab at said one side edge, said mask being removed from areas underlying said slab to allow liquid to flow to said slab.

* * * * *